United States Patent [19]
Annis

[11] Patent Number: 5,179,581
[45] Date of Patent: * Jan. 12, 1993

[54] AUTOMATIC THREAT DETECTION BASED ON ILLUMINATION BY PENETRATING RADIANT ENERGY

[75] Inventor: Martin Annis, Cambridge, Mass.

[73] Assignee: American Science and Engineering, Inc., Cambridge, Mass.

[*] Notice: The portion of the term of this patent subsequent to Jun. 4, 2008 has been disclaimed.

[21] Appl. No.: 710,046

[22] Filed: Jun. 4, 1991

Related U.S. Application Data

[63] Continuation-in-part of Ser. No. 406,333, Sep. 13, 1989, Pat. No. 5,022,062.

[51] Int. Cl.⁵ .......................... G01N 23/04
[52] U.S. Cl. .................... 378/57; 378/86; 378/87; 382/18; 382/41; 382/51; 250/442.1; 250/472.1; 358/111
[58] Field of Search ............ 378/56, 57, 86, 87, 378/88, 99, 901; 358/111; 382/16, 18, 41, 51; 250/442.1, 472.1

[56] References Cited

U.S. PATENT DOCUMENTS

| | | | |
|---|---|---|---|
| 4,031,545 | 6/1977 | Stein | 378/57 |
| 4,799,247 | 1/1989 | Annis | 378/87 |
| 5,022,062 | 6/1991 | Annis | 378/86 |

Primary Examiner—Janice A. Howell
Assistant Examiner—Kim-Kwok Chu
Attorney, Agent, or Firm—Pollock, Vande Sande & Priddy

[57] ABSTRACT

Automatic threat detection in association with imaging which relies on a backscatter detector and illumination by a flying spot source of penetrating radiation. The digital backscatter image is processed to produce a histogram. The histogram is compared to a predetermined threat characteristic and an alarm is sounded if the histogram exceeds the threat characteristic. The threat characteristic is derived in an empirical fashion and automatically modified based on sensing selected parameters associated with the scanning. Operator control over the threat characteristic is also implemented. The flying spot source is also associated with a transmit detector to produce a transmit image. The transmit image is also processed against predetermined parameters for threat assessment. The predetermined parameters are also operator variable.

12 Claims, 5 Drawing Sheets

AUTOMATIC THREAT DETECTION BASED ON ILLUMINATION BY PENETRATING RADIANT ENERGY

RELATED APPLICATION

This application is a continuation-in-part of applicant's co-pending application Ser. No. 406,333, filed Sep. 13, 1989, now U.S. Pat. No. 5,022,062.

FIELD OF THE INVENTION

The present invention relates to threat detection assessment based on illumination of an object by penetrating radiant energy.

BACKGROUND ART

It has long been a goal in the field of object inspection to provide for automatic threat detection. A substantial advance in this art is the system described in the Stein et al U.S. Pat. No. 4,031,545 entitled "Radiant Energy Alarm System". However, the Stein et al patent is limited to responding to a high level of opacity, which is typical of dense material (such as a metal) and thus has limited utility for detecting less opaque objects which include explosives, plastics, narcotics, drugs, etc.

Backscatter imaging has been known at least since the Stein publication, "Flying Spot X-Ray Imaging Systems", which appeared in Vol. 30, No. 7 (Jul. 1972) of *Materials Evaluation* (pp. 137 et seq).

A further advance was made in respect of imaging such less opaque objects like plastic or explosives or the like by the introduction of American Science and Engineering's "Z" system; see for example "A New X-Ray Scanner to Hinder Hijackers", *Fortune*, Apr. 28, 1986, page 146 and U.S. Pat. No. 4,799,247.

However, the significant difference between the response of less dense materials (such as plastics, drugs, etc.) to x-ray illumination and the response of highly dense material (such as metal) to the same illuminating radiation renders problematical application of the techniques in U.S. Pat. No. 4,031,545 for detection of threats posed by low Z objects. More particularly, the techniques of U.S. Pat. No. 4,031,545 are based on detecting very dense objects. How those techniques could be used in processing x-ray signals generated by less dense material is not apparent. For example, the presence of metal per se is not necessarily correlated with a degree of threat; in the case of a metal object, it is the shape of the object which is significant. Because of the significant difference in transmissivity between metals and nonmetals, in the presence of a metal in an x-ray image, not only is the presence of the metal readily detectable, but the shape of the metal object is also readily discernable. Thus, the technique described in U.S. Pat. No. 4,031,545 finds utility in merely calling the operator's attention to a region of high density. Since the shape of the high density object is usually readily recognizable, the operator can quite readily determine whether or not the object poses a threat. On the other hand, explosives do not usually carry any particular shape, rather it is the mass or volume of the explosive (as opposed to its shape) which determines the degree of threat. It is not apparent from publications on transmission imaging that mass or volume of low density material can be differentiated.

SUMMARY OF THE INVENTION

The intensity of the backscatter signal has been determined to be a function not only of the opacity (or density) of the non-metal object producing the scatter, but also its thickness. By itself, this is not a useful characteristic since the attacker can, by increasing the area of the explosive material at the same time reduce its thickness, without changing its volume or mass. Accordingly, the absolute intensity of the signal scattered from any particular point of the object is not, by itself, determinative of the degree of threat posed by the object. Stated in other terms, while a very thick low Z object (resulting in a given scatter intensity) of a given area could be considered a threat, the same threat could be exhibited by a thinner object (with scatter intensity less than the given intensity) of greater area. At the same time, many objects which are inspected include objects with opacity similar to explosives but which pose no threat at all. Thus, any threat detector which was designed to ensure that objects that passed had a minimal probability of threat would at the same time result in many false positive threat detections. On the other hand, merely increasing the backscattered signal intensity threshold that was required before threat detection was initiated would mean increasing the extent of false negatives, i.e. allowing high threat objects to pass undetected. Thus there is a need on two fronts. A first requirement is the ability to monitor backscatter signal intensities which, while relatively common, at the same time are significant enough so that if a large area of an object with this intensity were encountered a real threat could be present. A second, correlative requirement, that there be some technique to distinguish real threats from an object with a similar back scatter signature but which is no threat at all. At the same time it must be recognized that the first requirement does not define a single threshold (a given number of pixels with intensity exceeding a fixed level) since the attacker can trade off frontal area and signal intensity by merely properly molding the explosive volume into different areas and thicknesses. Thus the first requirement, properly taken into account, translates into monitoring a broad area in the plane of pixel intensity and area (number of pixels) showing that intensity.

The invention is arranged to reliably detect the threat probability for an object based on signals produced by illuminating the object with penetrating radiation. While advantages accrue from using embodiments of the invention which include at least a backscatter detector, the processing which is described herein produces significantly more information than found in the prior art, both from signals derived from a backscatter detector as well as from signals derived from a transmission detector.

The flying spot scanner provides the ability to map, at any given instant, the signal intensity output by the detector (either a scatter or a transmit detector) into a fixed region of the object. Using this mapping the apparatus monitors the detector output at any instant and converts the output to digital form (A/D conversion). The digital signal (or the digital value obtained by the A/D conversion) or a group of time adjacent digital signals (suitably averaged or combined) can be considered a pixel, an elementary portion of the image that will be produced, and at the same time one of a large number of input values which will be processed to detect threat probability.

If there were a single intensity threshold (for signals from a backscatter detector) which reliably distinguished threats from non threats it would be possible to simply ignore all pixels below the threshold and merely monitor those pixels above the threshold. However there is not such a single threshold, rather there is a broad band of pixel intensity values which are monitored. To a first approximation, for a given intensity level there is demarcation between threat probability and non threat probability which depends on the extent of the given intensity; i.e, over what area is the intensity above the given intensity. Thus the digital pixels (produced by the A/D conversion of the detector output) can be processed to produce a histogram exhibiting, for each pixel intensity within the band being monitored, the number of pixels showing at least that intensity. Probable threats are distinguished from non threats using two techniques in concert. The first technique is to establish a characteristic which defines a limiting value for each pixel intensity, if the histogram shows a number of pixels (area) in excess of the characteristic for the same intensity then the object merits the operators attention, and an alarm is enabled to draw the operators attention to the result of the processing. The second technique is a visual inspection by the operator.

In accordance with one embodiment of the invention, an object is passed through a field illuminated by a flying spot of penetrating radiation. The x-rays scattered from the object are detected (in a backscatter detector) and processed. Preferably, the analog output of the backscatter detector is converted to digital form. As the object passes through the field illuminated by the flying spot of penetrating radiation, the backscatter detector produces a sequence of signals representing the scattering characteristics of the object. The sequence of signals, after analog-to-digital conversion, can be interpreted as a sequence of pixels where each pixel can be mapped to an identifiable region of the object. The pixel-representing digital values are input to a digital computer. As the sequence of pixel-representing signals are input, they are stored and the computer performs a histogram computation. The histogram procedure which is employed in an embodiment actually constructed can be referred to as a cumulative histogram. The cumulative histogram determines, at a representative pixel intensity, the number of pixels of greater intensity than the representative intensity. As will be described the use of a cumulative histogram is not essential to the invention and a differential histogram can also be employed. In what has been referred to as an differential histogram the region of pixel intensity is divided into a number of intensity bands, each band has an upper and lower bound. The differential histogram determines, for any given band, the number of pixels whose intensity lies between the upper and lower bound. In use of the differential histogram the different intensity bands need not be contiguous, although they could be.

The computer also has established (by means which will be described) a two-dimensional characteristic which, if plotted on a graph of number of pixels vs. intensity values, has the form (for use with the cumulative histogram) of a monotonically decreasing limiting value.

The plot of this characteristic may be a smooth curve although that is not essential to the invention. After scanning of the object has been completed, and the histogram is available; the histogram is compared to the limiting characteristic. If at any point, the value of the histogram for that band exceeds the characteristic value, then an alarm function is performed to inform the operator that an object with a high threat probability has been detected.

This feature of the invention, i.e. using a limiting characteristic over a relatively large range, effectively matches the realistic threat in the case of explosive. The threat capability of an explosive is not solely related to the frontal area, nor is it solely related to the thickness of the explosive component. Rather, the threat capability of an explosive is related to the mass or volume of the explosive. In other words, an explosive of frontal area A and thickness T has substantially equivalent threat characteristics to an explosive of frontal area A/2, if at the same time the thickness is 2T.

It turns out that the intensity of the backscatter signal depends not only on the density (atomic number) of the material, but its thickness as well. In other words, a material with a given density (or atomic number) D will in one thickness produce a backscatter signal of a given intensity, but if that same material is present in a thicker form, the intensity of the backscatter signal is increased.

The foregoing should make it clear that threat detection systems which respond only to pixel values of a fixed lower intensity are susceptible to being "fooled" by explosive material which has been purposely molded in a "thin" form designed to produce a backscatter signal of intensity less than the fixed threshold. This limitation on threat detection capability is reduced by using a limiting characteristic which is defined over a large range of intensities.

The invention overcomes the foregoing problems by weighting the threat contribution factor of any particular portion of the object based on that combination of opacity and thickness which is reflected in the intensity of the backscattered signal.

The actual threat characteristic which is employed can be derived experimentally from scanning many typical objects, including objects both with and without threats or simulated threats. For simplicity a "standard" object is used, with standard parameters, such as frontal area and distance from the backscatter detector. The experimentally derived threat characteristic is then directly usable for objects with parameters substantially similar to the standard parameters.

Whether or not the object being scanned substantially corresponds to the standardized objects can be automatically detected. Distance of the scanned object from the backscatter detector is measured for comparison with the standard distance. Variations of this distance are automatically handled as will be described. Likewise the actual frontal object area is measured and any difference between actual and standard area is determined. Area variations are automatically handled as will be described.

Scanning distance (between scanned object and the backscatter detector) is measured by any conventional distance detector, in the embodiment actually constructed a sonic detector was used. The measured distance is an input to the processing. Since changes in distance between object and the backscatter detector produce predetermined changes in backscatter intensity the variation in distance from the standard object/backscatter detector distance can be, and are related to intensity variations. As a result the actual backscatter intensity is normalized to equivalent backscatter intensity at the standard distance.

The actual frontal area of the object being scanned is determined from the number of pixels whose backscatter intensity exceeds some low threshold. This number of pixels can be related to variations of frontal area of the scanned object from the standard frontal area. One axis of the threat characteristic is number of pixels. Any value along this axis (number of pixels) can be related to some portion or per cent of the total frontal area, by simply obtaining a ratio of that number of pixels to the number of pixels corresponding to the total frontal area; therefore the threat characteristic axis can be converted to per cent of frontal area. In this way the processing automatically handles scanning objects whose frontal area differs from the standard frontal area.

In addition to automatically handling these variations of the scanned object from standard parameters, the threat detector of the invention also enables the operator to tune the sensitivity of the system by "manually" changing the threat characteristic relative to the standard threat characteristic; this allows the operator to vary the probabilities of detection. The operator can, by inputs to the system move the threat characteristic parallel to the pixel intensity axis, parallel to the number of pixel axis or by any combination of the foregoing which effectively moves the threat characteristic diagonally relative to these axes.

Thus in accordance with the invention the processor receives digital values (pixels) representing scatter intensity from an A/D converter. The processor produces a pixel map or image of the scanned object where each point represents scatter intensity. In an embodiment actually constructed each pixel was digitized to 8 bit accuracy. The processor also performs a (cumulative) histogram process by counting, for each of the different 256 pixel values, the number of pixels of intensity greater than the pixel value. Thus the histogram can be represented in two dimensions, pixel intensity along one axis and pixel number along the other axis. Alternatively to perform a (differential) histogram the processor would merely count, for each of the 256 pixel values, the number of pixels at that intensity. The differential histogram is similarly two dimensional. The processor then compares the histogram with a predetermined limiting characteristic; if the histogram is greater than the limiting characteristic an alarm is sounded to alert the operator to the presence of threat. In addition, to assist the operator in viewing the image to determine whether the threat merits a physical inspection, selected portions of the image are flashed. When a histogram exceeds the limiting characteristic it does so at one or more values of intensity. Pixels at or greater than this intensity are flashed to show the operator the shape or distribution of the threat.

The limiting characteristic is experimentally defined for standard objects scanned at a standard position. Corresponding parameters of the object actually scanned are detected and compared to the standard parameters; differences can be handled by compensation. Backscatter intensity is reduced as the distance between scanned object and detector are increased. The actual object/detector distance is measured. Based on a comparison between measured and standard distance either the detected pixel intensity value can be modified to conform to the standard distance or the limiting characteristic can be modified to conform to the measured distance. The actual object frontal area can also be measured and compared to standard object frontal area. While one axis of the limiting characteristic is number of pixels, this axis can be converted to per cent of frontal area since the standard object is also associated with a standard number of pixels. With this technique the actual image can be modified for the difference between actual frontal area and standard frontal area or the limiting characteristic can be modified for the same difference.

In addition to processing the signals derived from a backscatter detector as just described, the present invention also provides for processing, in a similar manner, signals derived from the transmit detector. More particularly, the signals derived from the transmit detector can be used to create an image of the object as is conventional in the prior art. However, in addition, the signals from the transmit detector are processed to create an intensity distribution or histogram for the signals from the transmit detector. Typically, the signals from a transmit detector reflect the intensity of the illumination beam as it reaches the detector.

Accordingly, the illumination beam reaching the transmit detector which has traversed only air is relatively high, whereas the intensity of the beam reaching the detector which has traversed, for example, a thick metal object is relatively low. It is sometimes convenient, however, to transform these signals into signals which represent absorption or attenuation. Signals transformed into signals representing absorption and/or attenuation exhibit the inverse characteristic. More particularly, there is relatively little or no absorption or attenuation for energy traversing only an air space, whereas the attenuation and/or absorption for energy traversing a relatively thick object would be relatively high. Just as in the case for the backscatter originated signals, the histogram based on attenuation and/or absorption from the transmit detector can be compared to a standard or reference and deviations can be used to trigger an alarm to call the operator's attention to the object. While this description has referred to processing signals based on attenuation and/or absorption, it should be emphasized that the transformation is not an essential characteristic of the invention. Histograms can be produced from signals representing transmitted intensity and compared with an appropriate standard or reference for the same purpose. The advantage of describing the invention in terms of transformed signals is that the histogram of the transformed signals is generally similar to the histogram of the backscattered signals.

Accordingly, the invention comprehends illuminating an object with penetrating radiant energy, detecting signals transmitted through the object, creating a histogram or intensity distribution, comparing the histogram or intensity distribution against a standard or reference and initiating an alarm based on that comparison. The invention further comprehends a method and apparatus as just described which further includes detecting energy scattered from the object, creating a histogram or intensity distribution from the signals generated by scattered energy, comparing the histogram based on scattered energy against a threat characteristic and enabling an alarm dependent on that comparison.

BRIEF DESCRIPTION OF THE DRAWINGS

FIGS. 3 and 4 are graphs of a typical limiting threat characteristic plotted with number of pixels on the ordinate and pixel intensity on the abscissa; FIG. 4 also shows superimposed the comparison of two histograms based on backscatter signals both evidencing a threat;

DETAILED DESCRIPTION OF PREFERRED EMBODIMENTS

Figure 1:
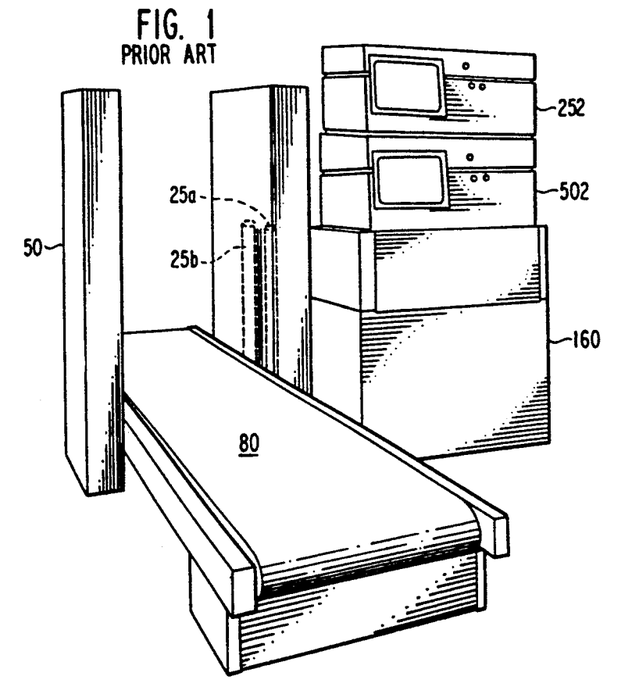
FIGS. 1 and 2 (similar to FIGS. 1 and 2 from U.S. Pat. No. 4,799,247) show respectively a perspective view of the apparatus implementing the present invention and an exploded view showing generation of the flying spot 30 and the front or transmit detector 50 and the backscatter detector 25.
Figure 2:
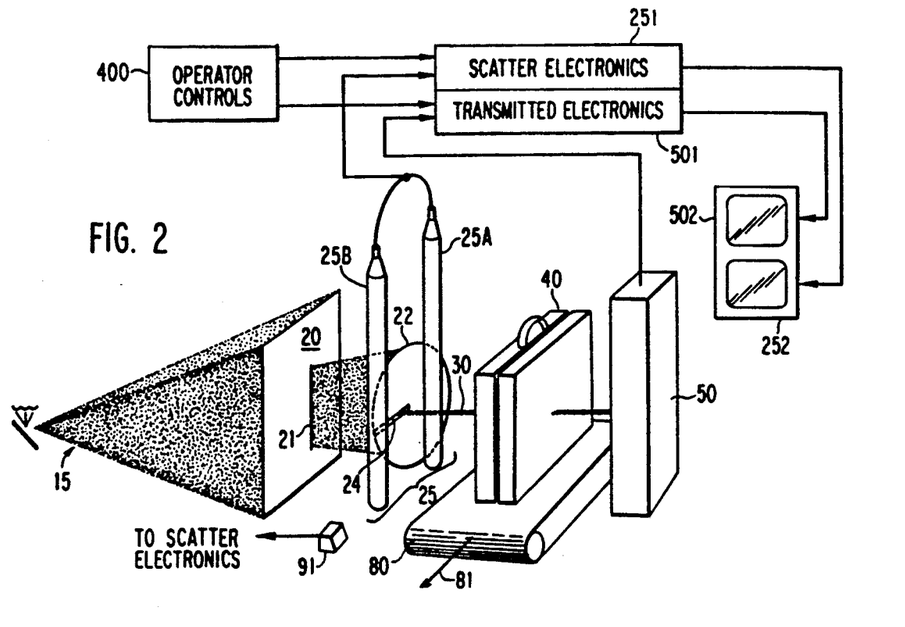

FIGS. 1 and 2 are, respectively, a three dimensional view and an exploded view of the apparatus in implementing American Science and Engineering's Model Z equipment and is more completely described in U.S. Pat. No. 4,799,247. The automatic threat detection capability of the present invention is implemented in part by the scatter electronics 251 and in part by the transmitted electronics 501. As is described in U.S. Pat. No. 4,799,247, both the transmitted and scatter electronics may include apparatus to perform analog-to-digital (A/D) conversion of the respective detector output as well as digital storage of the resulting converted digital values. In accordance with the present invention the transmitted and scatter electronics includes, in addition to the foregoing, apparatus to perform a histogram procedure as will be described below. The scatter electronics 251 also includes apparatus to establish a limiting characteristic and perhaps apparatus for modifying that limiting characteristic and for comparing the histogram to the limiting characteristic, as will also be described. The transmitted electronics 501 further includes apparatus to establish a standard or reference characteristic and perhaps apparatus for modifying that standard or reference characteristic and for comparing a transmit based histogram to the standard or reference characteristic, as will also be described.

Referring to FIGS. 1 and 2, the flying spot scanner located between the backscatter detector 25 (comprising backscatter detector elements 25A and 25B) includes a plate 20 with a slit 21 therein, a chopper wheel 22 with a radially directed slit 24 so that when an x-ray source is energized, the source produces radiation 15 which impinges on the plate 20. The radiation passing the plate 20 is in the form of a fan beam, as shown in FIG. 2. The fan beam impinging on the rotating chopper wheel 22 produces the flying spot pencil beam 30 which repeatedly sweeps up along the transmit detector 50 and passes through an object such as the object 40 which is transported past the source and detector arrangement by the conveyor 80. Sonic detector 91 measures the distance from detector 25 to the object 40. The measured distance is an input to the scatter electronics for reasons described elsewhere. As the pencil beam 30 illuminates the object 40, the penetrating radiation is attenuated and the attenuated radiation reaches the detector 50. The detector 50 converts the attenuated radiation beam into an electrical signal which is input to the transmitted electronics 501. At the same time, the object 40, or more particularly the components contained within the object 40, also scatter x-radiation. Some of the scattered radiation which is scattered back in the direction of the source impinges on the backscatter detector 25. Scattered radiation impinging on the detector 25 is converted into an electrical signal which is input to the scatter electronics 251.

The source and detector arrangement which is described in FIGS. 1 and 2 has the characteristic that the signals in any instant in time produced by either the detector 50 or the backscatter detector 25 can be mapped to a particular region of the object 40 whose illumination produced the resulting signal. Accordingly, as those skilled in the art are aware, a signal, or a group of signals (suitably averaged or combined) can be used to represent a pixel, an elementary portion of an image that will be formed and displayed. The pixel, or the signal which is generated to produce the pixel, has an amplitude or intensity. In the case of the transmitted beam, detected by the transmission detector 50, the intensity of the pixel can be used to represent the attenuation presented to the illumination beam by the portion of the object 40 which was illuminated when the pixel was generated. By like token, the intensity of the pixel generated by the backscatter detector can be mapped to that region of the object 40 whose illumination by the penetrating pencil beam 30 produced the backscattered x-rays which generated the pixel.

The backscatter signal intensity is dependent on a number of variable factors (it is also dependent on the energy level of the illumination source, but since that will be reasonably constant, we can ignore this parameter). The backscatter signal intensity depends on the density along the line of sight of the pencil beam 30, the distribution of that density along that line of sight and the distance between each elemental mass and the backscatter detector 25. More particularly, both high Z and low Z components of the object 40 produce both attenuation and scatter. However for certain object thicknesses, high Z objects, the attenuation is more pronounced than scatter whereas, again for a reasonable range of thicknesses, for low Z objects, scatter predominates over attenuation. Furthermore, the intensity of the backscatter signal for a given low Z object also varies (non-linearly) with thickness. In other words, as the thickness increases, the backscatter signal will also increase. As those skilled in the art are aware, the backscatter intensity is also dependent on density. As a result, variations in density in the line of sight of the pencil beam 30 produce variations in the backscatter intensity. To the extent that the mass within the line of sight has a both constant thickness and density, the backscatter signal intensity will also remain relatively constant, whereas if the line of sight density and thickness varies, the backscatter signal intensity would also vary.

Threat detection is based on two criteria. In the first place, a threat characteristic is experimentally established over a relatively broad range of backscatter signal intensities or pixel values. The threat characteristic (for the cumulative histogram) is a monotonically decreasing line of demarcation when plotted in a plane of number of pixels vs. pixel intensity, as is seen for example in FIG. 3. The threat characteristic can be stored in the scatter electronics 251 in any convenient manner, such as for example a table of number of pixels for each of a plurality of pixel intensity values; modification of the threat characteristic is described below. As the object 40 is conveyed past the source and detectors, the backscatter detector 25 produces a sequence of analog signals which are converted into a sequence of digital values or pixels. The scatter electronics 251 performs a histogram processing on the pixels. When the entire object has been scanned, the resulting histogram is compared against the threat characteristic at each of a plurality of pixel intensity values. If at any one of these values the histogram produced by scanning the object and processing the pixels exceeds the threat characteristic for the corresponding pixel intensity, then a first criterion of threat processing is satisfied.

Figure 3:
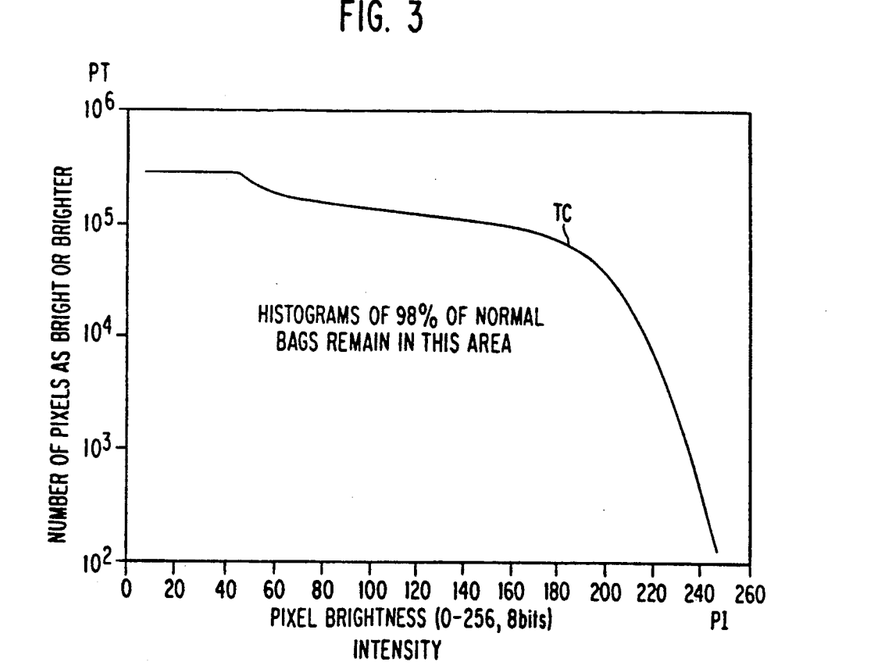

It should be understood that use of the threat characteristic as shown in FIG. 3 is a significantly more comprehensive technique than the processing described for the transmission signal in U.S. Pat. No. 4,031,545. Rather than establishing a single threshold for pixel intensity, as is described in U.S. Pat. No. 4,031,545, the threat characteristic of FIG. 3 establishes a broad range of pixel intensities which are monitored, and within this range, for each value of pixel intensity, there is a corresponding number of pixels. If the number of pixels for any pixel intensity within the range over which the threat characteristic is defined exceeds the number of pixels or threat characteristic, then a first criterion of threat detection has been satisfied.

Satisfying the first criterion produces an alarm, which may be an audible or visual alarm, which is enabled by the scatter electronics 251. Enablement of the alarm initiates the second criterion of threat detection—the visual observation of the resulting display by the operator.

Use of the second criterion, the operator's visual scan of the display, reduces the frequency of false positives, and this allows a broader range of pixel intensities to be monitored so as to limit the number of false negatives.

More particularly, false negatives are instances in which a real threat is missed; the need to reduce or eliminate the possibility of false negatives should be apparent. One constraint on establishing the parameters of the threat characteristic (for example FIG. 3) so as to minimize or eliminate false negatives, is the number of false positives. A false positive require the physical examination of an object because it has triggered the threat system, even though a later physical inspection shows no threat at all. While minimizing or eliminating false negatives is important, it is not practical to minimize or eliminate false negatives by increasing the number of false positives, since false positives slow the processing of objects to be scanned and thus limits the overall accuracy of the process.

The operator is instructed, when an alarm is enabled as described above, to view the display. The backscatter display will show various intensities over the area occupied by the object and the region that triggered the alert will be shown as flashing.

Figure 4:
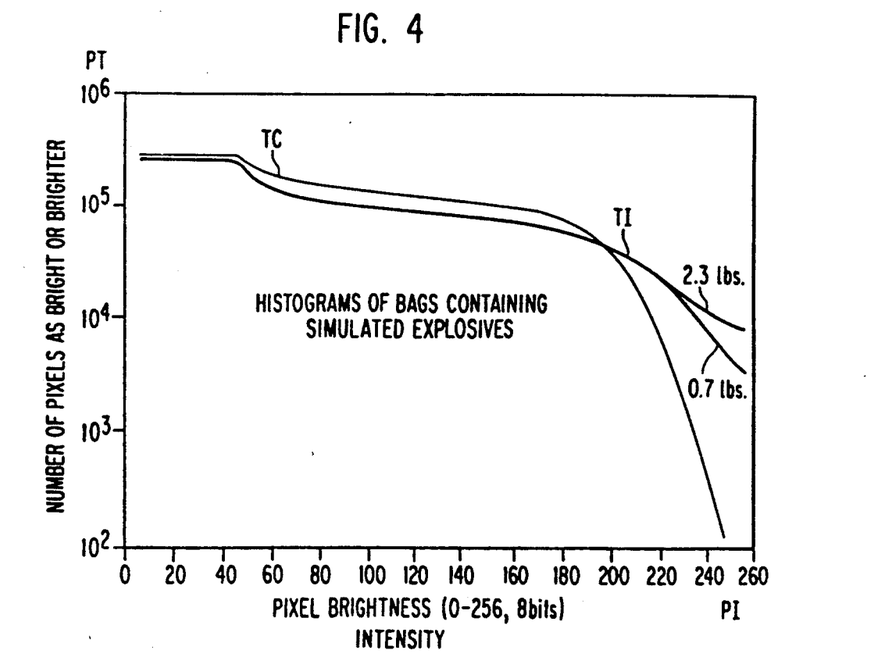

FIG. 3 shows a monotonically decreasing threat characteristic TC plotted in the plane of number of pixels vs. pixel intensity. The region of this plot below TC is a non-threat region, whereas the region above TC is a threat region. FIG. 4 is similar to FIG. 3 but also shows two typical histograms which can be produced in accordance with the processing of backscatter signals. The histogram labelled 2.3 lbs shows that over the pixel intensity band which is monitored, in the region of the threat indication TI, there is a value of number of pixels for a given pixel intensity which exceeds the number of pixels of the threat characteristic TC. In other words, the histogram indicates a threat. The other histogram, labelled 0.7 lbs, also indicates a threat.

Figure 5:
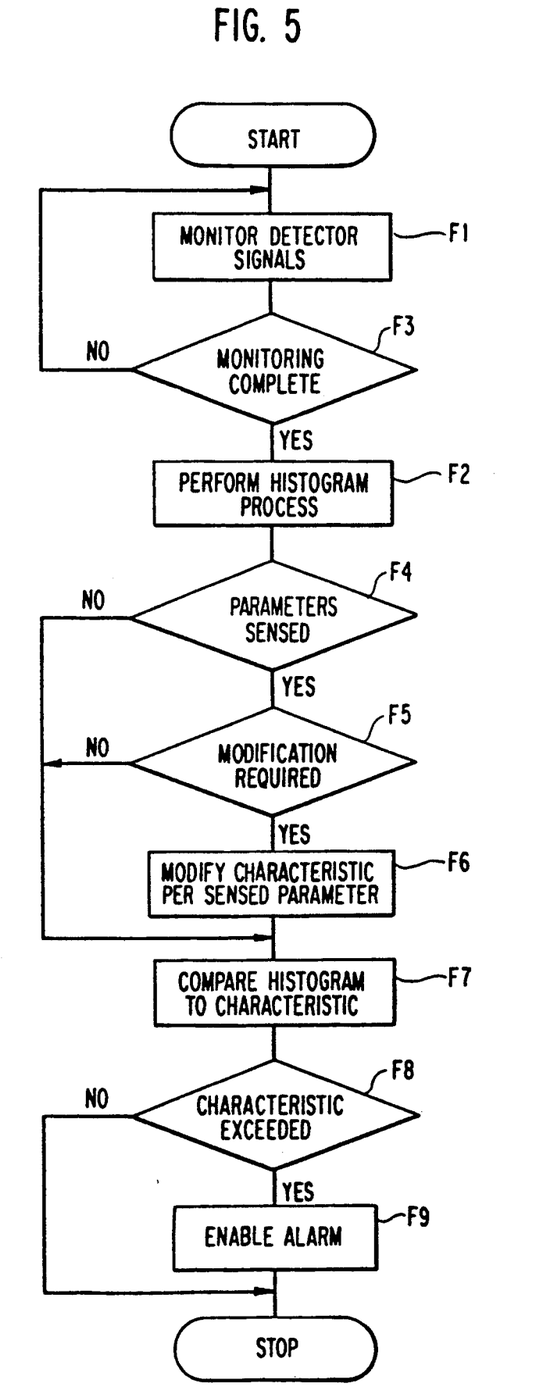
FIG. 5 is a flow chart of the processing implemented by the scatter electronics 251 in accordance with the present invention.

FIG. 5 shows the processing employed on backscatter signals. When processing is initiated, function F1 monitors the output of the backscatter detector 25. The monitoring function includes analog-to-digital conversion and storage. The digital pixel values are then used (F2) to perform a histogram process to create a histogram such as those shown in FIG. 4. Function F3 determines whether or not monitoring (analog-to-digital conversion and histogram processing) has been completed. Completion of processing can be detected in any one of a number of conventional ways. For example, conventionally baggage scanning equipment includes photocells to detect when an object supported on the conveyor 80 approaches the source/detector to initiate processing. By like token, another photocell is used to detect when the object has passed completely beyond the source/detector. The output of this detector can be used to determine that processing is complete. Alternatively, absence of an output from the backscatter detector for a predetermined period of time can also be used as an indication that the object has completely passed the source/detector region to indicate that processing is completed. Functions F4–F6 will be described below. Briefly, these functions allow the threat characteristic TC to be modified based on sensed parameters of the object being illuminated. For the present discussion, we will assume that no modification of the threat characteristic TC is required. Accordingly, function F7 is performed to compare the histogram which is produced by the processing of step F2 with the threat characteristic TC. There are many ways to implement this comparison. For present purposes, we can assume that the threat characteristic TC is actually defined by a table which gives a pixel threat number (PT) for each of a plurality of pixel intensities (PI). Function F7, in such a case, can be implemented by merely comparing at each of the pixel intensity (PI) values for which the table has a corresponding TP value, whether the histogram value is greater than or less than the PT value. Other conventional techniques will be apparent to those skilled in the art. When the comparison of step F7 is complete, then function F8 determines whether the threat characteristic (TC) value is exceeded by any histogram value for a given pixel intensity. If no histogram value exceeds the corresponding threat characteristic value, then processing has been completed and no threat has been detected. On the other hand, if at any pixel intensity value which is used in the comparison of step F7, the histogram value exceeds the threat characteristic (TC), then function F9 is performed to enable the alarm. As described above, the alarm is used to alert the operator that a further inspection is necessary. At the same time each pixel in the image, with intensity in excess of that pixel intensity whose number exceeded TC, is shown flashing. This gives the operator an understanding of the shape of the potential threat. Although not shown in FIG. 5, the apparatus produces a digital image of the scanned object from the digital values stored in function F1. Flashing an image or portions of an image is a conventional function once the pixels to be flashed are identified. The comparison function F7 will, in the course of the comparison identify the intensity value(s) at which the histogram exceeds the characteristic. It is those pixels which are shown flashing.

Functions F4–F6 will now be described. Assume that function F4 senses that the object to detector distance is 25% greater than the standard. This is an indication that the detected intensity will be reduced from the standard intensity by that factor associated with a 25% increase in the distance. Although, as described above compensation can be implemented in either processing of the detected intensity or in modification of the characteristic, we describe the latter process although it should be apparent that similar results can also be produced by processing the detected intensity. In order to compensate for the reduced intensity occasioned by the increased object to detector distance the intensity axis of characteristic is modified by reducing the nominal intensity by that factor associated with a 25% increase in distance. Thereafter the histogram is compared to the characteristic as modified in function F6. It should be apparent that a similar modification is effected in response to changes in object area. In other words assume that the standard object, with frontal area $A_1$, is represented in $N_1$ pixels and that an object that is scanned has a larger frontal area $A_2$, represented in $N_2$ pixels. In order to modify the standard threat characteristic to account for the larger frontal area the characteristic axis representing the number of pixels is modified so that instead of representing $N_1$ pixels it represents $N_2$ pixels.

Figure 6:
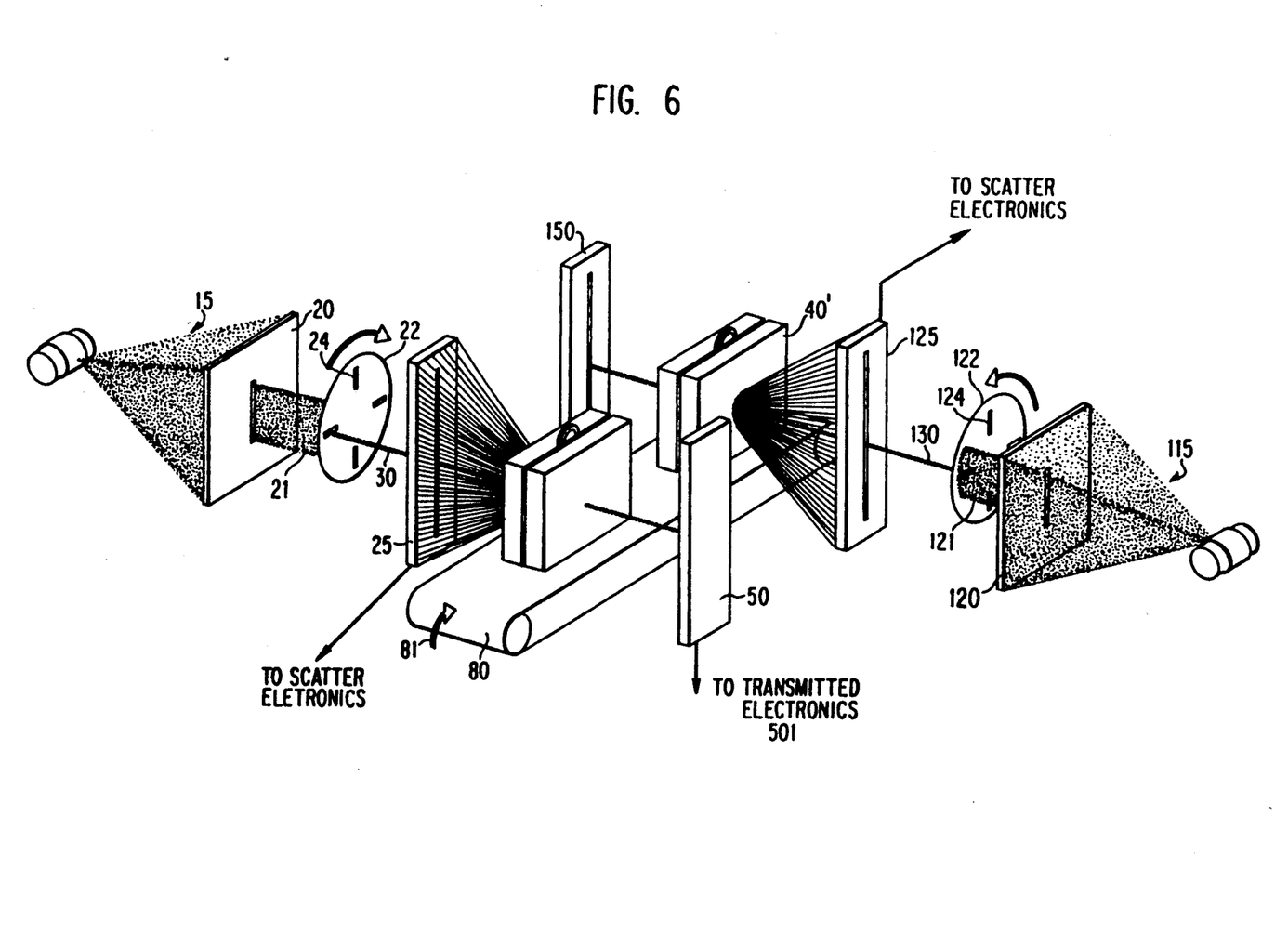
FIG. 6 is a schematic illustration of apparatus similar to FIG. 2 to which has been added a second source and detector pair in a configuration similar to American Science & Engineering's ZZ product.

FIGS. 1 and 2 relate to a system with a single backscatter detector. Since detected backscatter intensity is related to the distance between the scattering source and the detector the detector 25 will respond more effectively to scattering from that portion of the object closer to the detector than scattering from portions of the object further from the detector. One way of reducing the effect of this bias is to pass the object through the system twice so as to scan the object from different sides on the first and second pass. Another way to reduce the effect of this bias is to use two separate backscatter detectors, one on either side of the object as schematically shown in FIG. 6. The transmitted electronics is arranged to respond to one of the two transmit detectors to develop a transmit image. The backscatter electronics responds to both backscatter detectors to develop two backscatter images, each imaged from a different side. The backscatter electronics performs the histogram procedure, comparison and alarm function, if necessary, as described above on both backscatter images.

Figure 7:
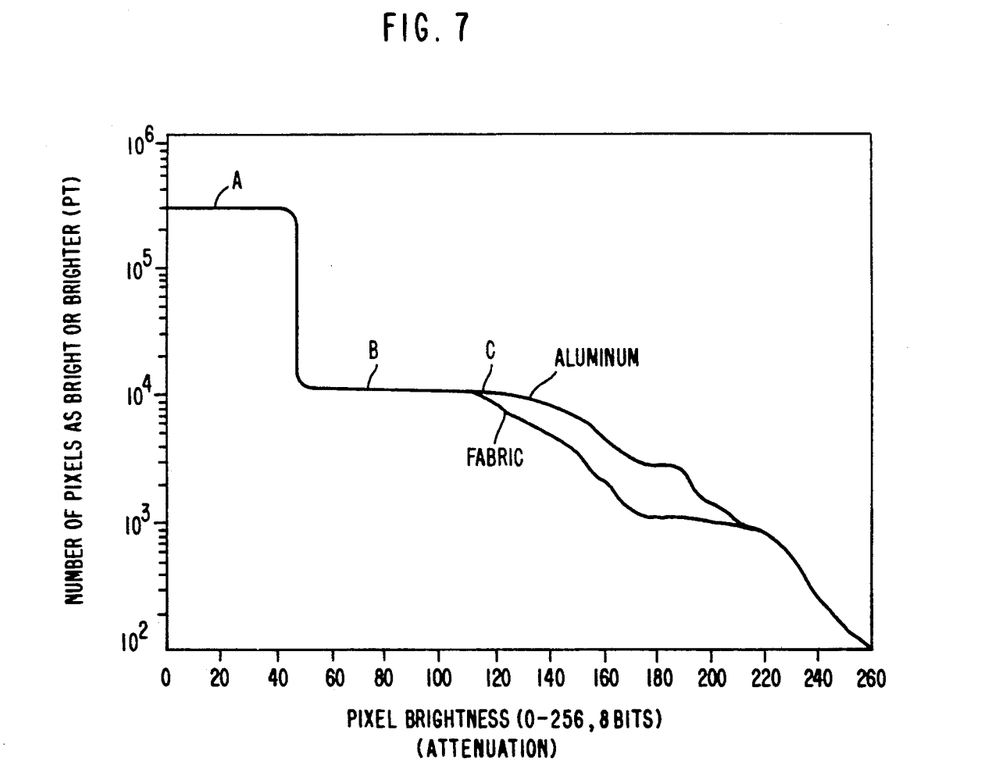
FIG. 7 plots a typical transmit signal based attenuation distribution or histogram, i.e. number of pixels with at least that attenuation vs. attenuation.

An important feature of the invention is the use of the signals from the transmission detector, along with the signals from the backscatter detector in order to provide the operator with more complete information about the contents of the object 40. FIG. 7 is a transmission histogram for a typical object that might be checked at an airport. FIG. 7 plots pixel brightness, representing attenuation (the higher the brightness, the higher the attenuation), vs. the number of pixels or the frontal area which has at least the brightness or attenuation or greater. FIG. 7 shows a first plateau, labeled A. This plateau covers the range of attenuation from zero up to the attenuation value for air. The plateau represents the fact that all pixels in the image have an attenuation which is equal or greater than the attenuation of air. FIG. 7 also shows a second plateau, labeled B. The higher plateau B represents the number of pixels which have an attenuation which is greater than the attenuation of air. FIG. 7 also denotes a point C, at which point the plot drops off from the level of the plateau B. The point C represents the thinnest portion of the object being scanned inasmuch as its attenuation is just slightly greater than that of the plateau B. FIG. 7, in the region to the right of the point C, shows two plots, one for an object having an aluminum skin, such as an aluminum suitcase, and another for an object having a fabric skin, such as a fabric suitcase.

Just as in the case for creating a threat characteristic for backscatter signal comparison purposes, a standard or reference transmit histogram can be created for the transmit histogram. The standard or reference characteristic of the (cumulative) histogram is a monotonically decreasing line of demarkation when plotted in a plane of number of pixels vs. pixel intensity, as seen for example in FIG. 7. The standard or reference characteristic is determined experimentally and, as suggested for example by the different plots shown in FIG. 7, a standard or reference characteristic can be created for aluminum objects on the one hand and fabric objects on the other hand. Having created the standard or reference characteristics, the characteristic or characteristics can be stored in the transmit electronics 501 in any convenient manner, such as for example a table of numbers of pixels for each of a plurality of pixel intensity values.

Having created the standard or reference characteristics for the transmit histogram, the processing for transmit signals can be similar or identical to that shown in FIG. 5. In the event there is more than a single standard or reference characteristic for the transmit processing, the appropriate standard or reference characteristic can be selected either manually automatically. Having selected the appropriate standard or reference characteristic, the processing shown in FIG. 5 operates on the transmit signals detected in order to create a transmit signal histogram such as that shown in FIG. 7. Thereafter, function F8 compares the histogram against the standard or reference characteristic, over a range of pixel intensities and enables an alarm when the transmit histogram exceeds that of the standard or reference characteristic.

In the event the alarm is enabled in response to function F8, all pixels in the conventional transmit image whose attenuation exceeds the value of attenuation at which the transmit histogram exceeded the standard or reference characteristic can be flashed to draw the operator's attention to the region in the object which has generated the alarm.

In a similar fashion the operator controls 400 allow the operator to vary the threat characteristic for backscatter processing and the standard or reference characteristic for transmit processing for the same purpose to change the sensitivity to objects of particular makeup. It should be apparent that at some point increasing the sensitivity decreases false negatives (which is desired) but also may increase false positives (which is not desirable). Allowing the operator to change the sensitivity then allows an optimum sensitivity to be arrived at by an empirical process. The threat characteristic (FIG. 3) can be varied by "moving" the line of demarkation parallel to the intensity axis (horizontally, left or right), parallel to the number axis (vertically, up or down) or both (diagonally). The operator controls 400 allows this action by expanding or contracting the threat characteristic (by a specified percentage) horizontally, vertically or both. The control can be implemented in any of the forms previously mentioned. Likewise, use of the operator controls 400 can be used to vary the sensitivity by shifting the standard or reference characteristic (for transmit processing) in an entirely similar manner.

It should be apparent that many changes can be made to the embodiment described herein within the spirit and scope of the invention. The invention should not be limited by the specific embodiment described herein but rather is to be construed from the claims attached hereto.

I claim:

1. An improved imaging system comprising:
   an illumination source comprising a flying spot of penetrating radiation;
   conveying means for transporting an object to be inspected through an inspection field swept by said flying spot of penetrating radiation;
   first radiation detecting means located to detect radiation passing through said object as the object is transported through said inspection field for developing a sequence of transmit signals representative of a sequence of transmitted radiation;
   processing means responsive to said sequence of transmit signals for determining whether or not said object is suitable for manual inspection, said processing means including:
   distribution means responsive to said sequence of transmit signals for determining transmit signal intensity distribution;
   means for comparing said transmit signal intensity distribution to a reference characteristic at each of a plurality of signal intensities; and
   alarm means for generating an alarm only if said transmit signal intensity distribution exceeds said reference characteristic for an intensity for which said characteristic is defined.

2. An improved imaging system as recited in claim 1 in which said distribution means includes means for producing a histogram.

3. An improved imaging system as recited in claim 2 in which said means for producing a histogram produces a cumulative histogram representing, for a given intensity, a number of transmit signals of intensity greater than said given intensity.

4. An improved imaging system as recited in claim 1 further comprising operator controlled means for changing said reference characteristic.

5. An improved imaging system for detecting concealed threats based on imaging by penetrating radiation comprising:
   an illumination source comprising a flying spot of penetrating radiation;
   conveying means for transporting an object to be inspected through an inspection field swept by said flying spot of penetrating radiation;
   first radiation detecting means, located between said illumination source and said conveying means, for detecting radiation scattered by an object transported through said inspection field and for developing a sequence of scatter signals representative of a sequence of scattered radiation;
   second radiation detecting means, located across said conveying means from said illumination source for detecting radiation transmitted by an object transported through said inspection field and for developing a sequence of transmit signals representative of a sequence of transmitted radiation;
   processing means responsive to said sequence of scatter signals and to said sequence of transmit signals for determining whether or not said object poses a threat, said processing means including:
   transmit signal processing means including distribution means responsive to said sequence of transmit signals for determining transmit signal intensity distribution;
   means for comparing said transmit signal intensity distribution to a reference characteristic at each of a plurality of signal intensities to determine if said transmit signal intensity distribution exceeds said reference characteristic;
   scatter signal processing means for processing said scatter signals against a scatter threat criterion; and
   alarm means enabled if either said transmit signal intensity distribution exceeds said reference characteristic or said scatter processing means determines said scanned object meets said scatter threat criterion.

6. An improved imaging system for detecting concealed threats based on imaging by penetrating radiation as recited in claim 5 wherein said scatter processing means includes:
   scatter distribution means responsive to said sequence of scatter signals for determining scatter signal intensity distribution;
   means for comparing said scatter signal intensity distribution to a threat characteristic at each of a plurality of signal intensities; and
   means for enabling said alarm means if said scatter signal intensity distribution exceeds said threat characteristic for an intensity for which said characteristic is defined.

7. An improved imaging system for detecting concealed threats based on imaging by penetrating radiation as recited in claim 6 which further includes operator controlled means to change at least one of said reference characteristic or said threat characteristic.

8. A threat detecting system as recited in any of claims 5-7 which further includes means for generating an image based on said transmit signals and a further image based on said scatter signals.

9. An improved method of imaging comprising the steps of:
   illuminating an inspection field with a flying spot of penetrating radiation;
   transporting an object to be inspected through said inspection field;
   detecting radiation passing through said object as the object is transported through said inspection field and developing a sequence of transmit signals representative of a sequence of transmitted radiation;
   determining whether or not said object is suitable for manual inspection, including the steps of:
   determining transmit signal intensity distribution from said sequence of transmit signals;
   comparing said transmit signal intensity distribution to a reference characteristic at each of a plurality of signal intensities; and
   generating an alarm only if said transmit signal intensity distribution exceeds said reference characteristic for an intensity for which said characteristic is defined.

10. A method of identifying a concealed threat using penetrating radiant energy comprising the steps of:
   (a) scanning an object with a flying spot of penetrating radiant energy;
   (b1) developing scatter signals representative of radiant energy scattered by said object in response to the scanning of step (a);

(b2) developing transmit signals representative of radiant energy transmitted by said object in response to the scanning of step (a);

(c1) producing an intensity distribution of said scatter signals developed in step (b1);

(c2) producing an intensity distribution of said transmit signals developed in step (b2);

(d1) comparing said intensity distributions of step (c1) to a threat characteristic defined for plural intensities;

(d2) comparing said intensity distributions of step (c2) to a reference characteristic defined for plural intensities (e) enabling an alarm when either (1) said comparing step (d1) indicates that said scatter intensity distribution exceeds said threat characteristic for at least one intensity for which said threat characteristic is defined, or (2) said comparing step (d2) indicates that said transmit intensity distribution exceeds said reference characteristic for at least one intensity for which said reference characteristic is defined.

11. A method as recited in claim 10 which includes the further steps of storing said threat characteristic and varying said stored threat characteristic prior to effecting said comparison of step (d1).

12. The method of any of claims 10-11 which includes the further steps of:

(f) producing transmit and scatter images from said transmit and scatter signals, respectively; and (g) selectively flashing portions of said images when said alarm is enabled.

* * * * *